(12) United States Patent
Goldfarb et al.

(10) Patent No.: US 8,952,061 B2
(45) Date of Patent: Feb. 10, 2015

(54) METHODS AND COMPOUNDS REGULATING THE ERYTHROID RESPONSE TO IRON DEFICIENCY

(71) Applicants: Adam N. Goldfarb, Charlottesville, VA (US); Loretta L. Delehanty, Charlottesville, VA (US)

(72) Inventors: Adam N. Goldfarb, Charlottesville, VA (US); Loretta L. Delehanty, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 13/680,325

(22) Filed: Nov. 19, 2012

(65) Prior Publication Data
US 2013/0072428 A1 Mar. 21, 2013

Related U.S. Application Data

(63) Continuation of application No. 13/273,345, filed on Oct. 14, 2011, now abandoned, which is a continuation of application No. 12/376,593, filed as application No. PCT/US2007/076546 on Aug. 22, 2007, now abandoned.

(60) Provisional application No. 60/903,598, filed on Feb. 27, 2007, provisional application No. 60/839,249, filed on Aug. 22, 2006.

(51) Int. Cl.
| | |
|---|---|
| *A61K 31/19* | (2006.01) |
| *A61K 38/18* | (2006.01) |
| *A61K 31/194* | (2006.01) |
| *G06F 17/30* | (2006.01) |
| *H04L 29/06* | (2006.01) |
| *H04W 12/08* | (2009.01) |
| *C07C 69/704* | (2006.01) |
| *C12Q 1/25* | (2006.01) |
| *H04W 80/08* | (2009.01) |

(52) U.S. Cl.
CPC ........ *A61K 31/194* (2013.01); *G06F 17/30867* (2013.01); *H04L 63/102* (2013.01); *H04W 12/08* (2013.01); *A61K 31/19* (2013.01); *C07C 69/704* (2013.01); *C12Q 1/25* (2013.01); *H04W 80/08* (2013.01)
USPC ............................................ 514/557; 514/7.7

(58) Field of Classification Search
USPC .................................................. 514/557, 7.7
See application file for complete search history.

(56) References Cited

U.S. PATENT DOCUMENTS

| | | | | |
|---|---|---|---|---|
| 6,779,468 | B1 * | 8/2004 | Gupta ........................... | 210/647 |
| 2005/0250754 | A1 * | 11/2005 | Stockham ..................... | 514/184 |

FOREIGN PATENT DOCUMENTS

| | | | |
|---|---|---|---|
| JP | 61218522 A | * | 9/1986 |
| KR | 20020095553 A | * | 12/2002 |

OTHER PUBLICATIONS

Xue et al. Anemia treatment in the pre-ESRD period and associated mortality in elderly patients. American journal of kidney diseases:the official journal of the National Kidney Foundation. Abstract. vol. 40, No. 6, pp. 1153-1161 (Dec. 2000).*

Sachimaru Seno. Neutral or weak alkaline, stable collodial solution of iron hydroxide. English Translation of document JP 61218522 pp. 1-11 (Sep. 29, 1986).*

Bullock, Grant C., et al., "Iron control of erythroid development by a novel aconitase-associated regulatory pathway", Blood, Jul. 8, 2010, vol. 116, No. 1, pp. 97-108.

Richardson, Chante, L., et al., "Isocitrate ameliorates anemia by suppressing the erythroid iron restriction response", Journal of Clinical Investigation, vol. 123, No. 8, Aug. 2013, pp. 3614-3623.

See C. Richardson, et al.,"Isocitrate ameliorates anemia by suppressing the erythroid iron restriction response", as cited by the editor in The Journal of Clinical Investigation/JCI.org/Impact/Aug. 2013, pp. 1-16.

* cited by examiner

*Primary Examiner* — Elizabeth C Kemmerer
*Assistant Examiner* — Regina M Deberry
(74) *Attorney, Agent, or Firm* — Rodney L. Sparks

(57) ABSTRACT

The present invention discloses the signaling pathway involved erythroid repression by iron deficiency. Further disclosed is anon-toxic small-molecule compound which potently reverses the erythroid repression caused by iron deficiency. The present invention further encompasses novel compounds for inhibition of red cell production, useful, for example, in the treatment of polycythemia vera, a malignancy causing uncontrolled red cell production. These inhibitory compounds also promote megakaryocytic lineage commitment and may therefore be useful for augmentation of platelet production. The present invention further discloses isocitrate reversal of iron deprivation.

16 Claims, 6 Drawing Sheets

METHODS AND COMPOUNDS REGULATING THE ERYTHROID RESPONSE TO IRON DEFICIENCY

CROSS REFERENCE TO RELATED APPLICATIONS

This application is a continuation application of U.S. application Ser. No. 13/273,345, filed Oct. 14, 2011, which is a continuation of U.S. application Ser. No. 12/376,593, filed on Feb. 6, 2009, which is a national stage filing of International Application No. PCT/US2007/076546, filed Aug. 22, 2007, which claims the benefit under 35 USC §119(e) of U.S. Provisional Application No. 60/839,249, filed Aug. 22, 2006, and U.S. Provisional Application No. 60/903,598, filed Feb. 27, 2007, which are hereby incorporated by reference in their entirety.

STATEMENT REGARDING FEDERALLY SPONSORED RESEARCH OR DEVELOPMENT

This invention was made with government support under Grant Nos. CA93735-01 and CA100057-01 awarded by the National Institutes of Health. The government has certain rights in the invention.

BACKGROUND

Iron deficiency is an extremely common cause of anemia. However, the pathophysiology of iron deficient anemia remains poorly understood. Unlike anemias associated with defects in globin or in porphyrin synthesis, iron deficiency anemia employs unique hematopoietic control mechanisms to prevent marrow erythroid hyperplasia and to increase platelet production. These control mechanisms most likely serve protective functions, preventing an erythroid drain on limited iron reserves and increasing hemostatic capability to limit hemorrhagic red cell loss.

Understanding hematopoietic control mechanisms in iron deficiency has clinical relevance for multiple reasons. For example, inappropriate function of these mechanisms interferes with the efficacy of erythropoietin treatment in patients with a variety of chronic anemias. Many of these patients are elderly individuals with debilitating anemias due to chronic renal failure, chronic inflammatory conditions, or malignancy. Erythropoietin provides an opportunity to ameliorate the anemia while avoiding the exposure risks of red cell transfusions. While iron supplementation may partially restore responsiveness, frequent problems may exist with either non-compliance in taking oral iron, poor intestinal absorption, inefficient marrow utilization of existing iron stores, iron overload, and risk of infection with associated with intravenous iron infusion. Thus, circumventing the hematopoietic control mechanisms in iron deficiency could offer a strategy for enhancement of erythropoietin efficacy. On the other hand, in patients with serious deficiencies of total body iron stores, inadvertent abrogation of this control mechanism could cause a lethal reallocation of iron away from vital cellular functions such as supporting mitochondrial oxidative phosphorylation. Knowing these control mechanisms may permit prospective identification of patients at risk for life-threatening drug reactions. Another clinical benefit may arise from harnessing these mechanisms for the treatment of neoplasia, in particular polycythemia vera. Rather than phlebotomy to induce iron deficiency, one could employ agonists designed to activate the hematopoietic control mechanisms in a more highly controlled manner, permitting rapid and effective modulation of the red cell mass. Finally, exciting new opportunities for manipulation of platelet production, either positively or negatively, will arise from understanding the mechanisms of iron-deficient thrombocytosis.

Accordingly, there is a need for compositions that overcome iron deficiency, diminish erythroid repression, and regulate platelet production. For example, there is a tremendous need for new approaches in boosting poor platelet recovery post chemotherapy, a common clinical problem for which no adequate treatments currently exist. Therefore, the methods and compositions of the current invention proffer such results through the use of isocitrate, isocitrate derivatives, citrate and other Krebs cycle metabolites, aconitase and aconitase inhibitors, and/or aconitase agonistic proteins, wherein the utilization of these compositions can provide a synergistic effect that leads to the manipulation of red blood cell and platelet production, depending upon the needs of the subject.

SUMMARY OF THE INVENTION

Iron deficiency causes the suppression of bone marrow production of red cells, known as erythroid repression. This phenomenon is responsible for the poor responses of numerous anemia patients to treatment with erythropoietin. As highlighted above, supplying iron in combination with erythropoietin has been used to partially restore responsiveness, but is associated with the several problems. Furthermore, targeted therapies to boost the efficacy of erythropoietin in patients with chronic anemias which are due to functional iron deficiency have not previously been described. Moreover, the mechanisms whereby iron deficiency suppresses erythropoiesis and enhances megakaryopoiesis have not been elucidated. Through the analysis of primary human blood cell precursors, we have identified the signaling pathway involved in erythroid repression by iron deficiency and designed compositions and methods for its treatment.

To dissect these regulatory mechanisms, we designed a novel experimental system in which primary human hematopoietic progenitors undergo ex vivo culture in media with defined iron levels. We optimized iron levels to recapitulate clinical iron deficiency anemia, i.e. selective impairment of erythropoiesis with enhanced megakaryopoiesis. We identified the main mechanism as repression of erythroid aconitase enzymes, preventing conversion of citrate to isocitrate. We identified the aconitase enzymes as the critical target in erythroid inhibition by iron deficiency signals, including iron deficiency anemia and anemia of chronic inflammation. In addition, we identified aconitase enzymes as the critical target in enhanced megakaryopoiesis associated with iron deficiency signals.

We found that supplying exogenous citrate, or other Krebs cycle metabolites such as 2-oxoglutarate, succinate, or fumarate, magnifies the effects of iron deficiency. By contrast, supplying exogenous isocitrate reverses the effects of iron deficiency, with recovery of erythropoiesis and loss of enhanced megakaryopoiesis. To optimize the in vivo efficacy of isocitrate, we synthesized esterified versions of isocitrate. We found that the methyl ester of isocitrate (MIC) was a potent stimulator of erythropoiesis under conditions of iron deficiency.

To further elucidate these regulatory mechanisms, we examined the potential role of HBLD2 (HESB-like domain containing protein 2), a protein that promotes the function of aconitase. We found that introduction of HBLD2 into human progenitor cells protects them from the effects of iron deficiency. This shows that expression of a protein that drives aconitase activity causes efficient red cell development to occur even in the face of iron deprivation. This experiment provides further biologic evidence on the basic importance of isocitrate in programming red cell development.

Thus, we have identified a novel means for enhancement of erythroid differentiation through provision of the small metabolite isocitrate. Through modifications of this compound, we have made derivatives with higher potency, in part due to increased cellular permeability. In addition, it will be possible to target the enzymes that eliminate isocitrate, isocitrate dehydrogenases, to cause accumulation of endogenous isocitrate in cells. The ability of isocitrate to augment the function of erythropoietin has utility for the treatment of patients with anemia, many of whom show suboptimal responsiveness to erythropoietin. Conversely, blocking the production of isocitrate in cells through compounds that inhibit the aconitase enzymes, such as aconitine, oxalomalate, and fluoroacetate, provides a means for suppressing erythropoiesis in patients with excess red cell production, as in polycythemia vera. In addition, the diminished isocitrate production is associated with increased production of megakaryocytic progenitor cells. Therefore, compounds inhibiting aconitase enzymes, such as oxalomalate, are useful for the augmentation of megakaryopoiesis and platelet production.

Accordingly, in one embodiment, the present invention provides compositions comprising isocitrate and isocitrate derivatives and methods of their use to bypass the aconitase deficiency associated with iron deficiency to restore erythropoiesis and diminish megakaryopoiesis in the setting of anemias associated with iron deficiency signals. These compounds may be used restore or enhance erythropoietin responsiveness in a variety of chronic anemias.

In another embodiment, the present invention provides compositions that directly inhibit aconitase activity, such as oxalomalate, or that mimic aconitase inhibition, such as citrate or other Krebs cycle intermediates or similar molecules, to downmodulate erythropoiesis.

In yet another embodiment, the present invention provides compositions that directly inhibit aconitase activity, such as oxalomalate, or that mimic aconitase inhibition, such as citrate or other Krebs cycle intermediates or similar molecules, to stimulate megakaryopoiesis or augment responsiveness to thrombopoietin in patients with thrombocytopenia.

In yet another embodiment, the present invention provides compositions comprising HBLD2 and agonists thereof, and methods of their use to bypass the aconitase deficiency associated with iron deficiency to restore erythropoiesis and diminish megakaryopoiesis in the setting of anemias associated with iron deficiency signals. These compounds may be used restore or enhance erythropoietin responsiveness in a variety of chronic anemias.

In yet another embodiment, the present invention provides a method of using erythroid citrate and isocitrate levels, and any related metabolites, as markers of functional iron deficiency.

In yet another embodiment, the present invention provides isolated nucleic acids comprising nucleic acid sequences encoding the peptides of the invention.

DETAILED DESCRIPTION OF THE INVENTION

Definitions

Figure 1:
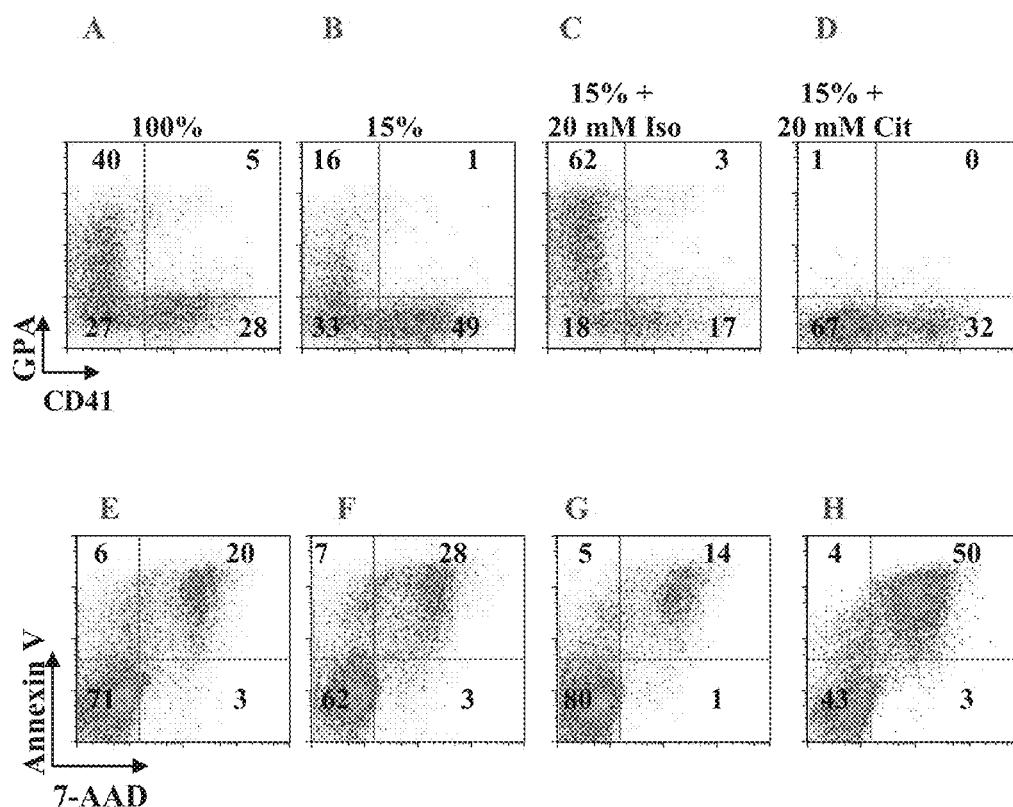
FIG. 1. Isocitrate but not citrate causes reversal of the effects of iron deficiency on erythroid development. A-D. Analysis of erythroid and megakaryocytic differentiation in erythroid cultures −/+ iron deprivation and −/+ isocitrate or citrate. Cells were cultured in erythroid medium in high iron (100%) or iron deprived (15%) conditions. Where indicated, the cultures were supplemented with 20 mM isocitrate (Iso) or 20 mM citrate (Cit). After 5 days of culture, the cells were harvested for flow cytometric analysis to determine surface expression of the red cell marker glycophorin A (GPA) or of the megakaryocytic marker CD41. Numbers inside the quadrants indicate the percentage of cells positive for either or both markers, by comparison with a negative control antibody. The analyses were carried out using a Becton Dickinson FacsCalibur flow cytometer and the FloJo (Treestar) software package. E-H. Analysis of the same cells as in A-D for death. The cells harvested after 5 days of culture were stained with FITC-Annexin V, which marks apoptotic cells, and 7-AAD, which marks all dead cells. Cells which mark only with FITC-Annexin V (upper left quadrant) are true apoptotic cells.

In describing and claiming the invention, the following terminology will be used in accordance with the definitions set forth below.

As used herein, the articles "a" and "an" refer to one or to more than one, i.e., to at least one, of the grammatical object of the article. By way of example, "an element" means one element or more than one element.

As used herein, the term "about" denotes being approximate or close a particular term, number, or numerical range. It is understood by persons of ordinary skill in the art that "about" may vary to some extent depending upon the context in which it is used. For example, given the context in which it is used, the term "about" may mean up to plus or minus 2%, 5%, or 10% of the particular term, number, or numerical range.

As used herein, the term "agonist" is intended to refer to an agent which increases the physiologic response of an organ or organism to the presence of a second agent. Agonists as used herein, may include, but are not limited to polypeptides, antibodies, and small molecules.

As used herein, an "analog" of a chemical compound is a compound that, by way of example, resembles another in structure but is not necessarily an isomer (e.g., 5-fluorouracil is an analog of thymine).

As used herein, the term "anemia" includes any disease, disorder, or condition characterized by, caused by, or related to any deficiency in the ability of blood to transport oxygen, deficiency in red blood cells, deficiency in hemoglobin, or deficiency in total blood volume. Anemia may be determined by comparing either hemoglobin (grams/deciliter), hematocrit (percentage of blood volume occupied by red blood cells) or red blood cell count (number of red blood cells times 10$^6$/μl) with "normal" values. These normal values are arbitrarily set as the mean±0.2 standard deviations of values in a healthy population. The normal ranges of blood parameters in adults are as follows: hemoglobin (gm/dl) 12.0-17.7; hematocrit (%) 36-52; Red blood cell count (number of red blood cells times 10$^6$/μl) 4.0-6.0; mean cell volume (fl) 80-100 (Adapted from Nathan, D. G. in *Cecil Textbook of Medicine*, (1992), J. B. Wyngaarden, L. H. Smith and J. C. Bennett, ed. W. B. Saunders Co., Philadelphia, pages 817-836, herein incorporated by reference). However, these normal ranges must be adjusted for persons living at altitude as well as for differences in race and gender.

Anemia may be masked by dehydration, where reduced plasma volume yields apparently normal hemoglobin concentrations, and likewise anemia can be mimicked by increased plasma volume, as in pregnancy. Thus the diagnosis of anemia can be made using published values as a guideline, but must be determined by a clinician skilled in the art.

Examples of "anemias" include, but are not limited to, anemias related to rheumatoid arthritis, anemias of infection and chronic inflammatory diseases, anemia of chronic kidney disease, anemia in the elderly, iron deficiency anemia, autoimmune hemolytic anemia, myelophthisic anemia, aplastic anemia, hypoplastic anemia, pure red cell aplasia and anemia associated with renal failure or endocrine disorders, megaloblastic anemias, defects in heme or globin synthesis, anemia caused by a structural detect in red blood cells, sickle-cell anemia, and anemias of unknown origins such as sideroblastic anemia, anemia associated with chronic infections such as malaria, trypanosomiasis, HIV, hepatitis virus or other viruses, and myelophthisic anemias caused by marrow deficiencies.

Anemias related to rheumatoid arthritis include, for example, anemia of chronic disease, iron deficiency anemia, and autoimmune hemolytic anemia. As used herein, the term "anemia of chronic disease" refers to an anemia which develops as a result of extended infection or inflammation. Certain chronic infections and inflammatory diseases cause several changes in the blood production (hematopoietic) system. These include a slightly shortened red blood cell life span and sequestration of iron in inflammatory cells called macrophages, resulting in a decrease in the amount of iron that is available to make red blood cells. In the presence of these effects a low to moderate grade anemia develops. The symptoms of the anemia may go unnoticed in the face of the primary disease.

Conditions associated with anemia of infection and chronic inflammatory diseases include such diverse diseases as chronic bacterial endocarditis, osteomyelitis, rheumatoid arthritis, juvenile rheumatoid arthritis, rheumatic fever, Crohn's disease, and ulcerative colitis.

As used herein, the term "citrate" refers to a citrate anion, in any form, including citric acid (citrate anion complexed with three protons), salts containing citrate anion, and partial esters of citrate anion.

As used herein, a "composition" refers to any mixture of two or more products or compounds. It may be a solution, a suspension, liquid, powder, a paste, aqueous, non-aqueous, or any combination thereof.

As used herein, a "compound" refers to any type of substance or agent that is commonly considered a drug, or a candidate for use as a drug, as well as combinations and mixtures of the above.

As used herein, "a compound of the invention" or "a compound of formula (I)" means a compound of formula (I) or a pharmaceutically acceptable salt, solvate, or physiologically functional derivative thereof. Similarly, with respect to isolatable intermediates, the phrase "a compound of formula (number)" means a compound of that formula and pharmaceutically acceptable salts, solvates and physiologically functional derivatives thereof.

As used herein, a "derivative" of a compound refers to a chemical compound that may be produced from another compound of similar structure in one or more steps, as in replacement of H by an alkyl, acyl, or amino group.

As used herein, a "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, are reduced.

As used herein, an "effective amount" means an amount sufficient to produce a selected effect.

As used herein, the term "erythropoiesis" refers to the proliferation and/or differentiation of erythroid precursor cells. Standard measures of erythroid cell proliferation and differentiation include hematocrit and reticulocyte counts. Hematocrit is a measurement of red blood cells, and is commonly expressed as the percentage of total blood volume which consists of erythrocytes. Reticulocyte counts measure 1-2 day-old cells that contain mRNA (absent in mature erythrocytes) and aggregates of ribosomes as demonstrated by staining (Erslev, A., "Reticulocyte Enumeration", in *Hematology*, McGraw-Hill, NY, 1990, herein incorporated by reference). A reticulocyte count is the percentage of such cells per 500 or 1000 cells counted. An average range for reticulocyte counts is 0.8% to 1.2%. EPO is commercially available (R & D Systems, Minneapolis, Minn. and Amgen, Thousand Oaks, Calif.) and activity is measured by calibration against the second international reference preparation of erythropoietin (Annable et al., 1972, *Bull. Wld. Hlth. Org.* 47: 99, herein incorporated by reference) using an in vivo assay which measures the incorporation of $^{56}$Fe into red blood cells of exhypoxic polycythemic mice (Cotes, et al., 1961, *Nature* 191: 1065, herein incorporated by reference) or by in vitro cell proliferation assay that uses a factor-dependent human erythroleukemic cell line, TF-1 (Kitamura, et al., 1989, *J. Cell. Physiol.* 140: 323, herein incorporated by reference).

As used herein, the terms "formula" and "structure" are used interchangeably.

As used herein, the term "fumarate" refers to a butenedioate moiety wherein the two ester carbonyl groups are oriented trans to one another. The term fumarate also includes fumiric acid. It is well known in the art that salts and esters of fumiric acid are known as fumarate.

As used herein, "homology" is used synonymously with "identity."

As used herein, the term "inhibit," refers to the ability of a compound of the invention to reduce or impede a described function, such as having inhibitory sodium channel activity. Preferably, inhibition is by at least 10%, more preferably by at least 25%, even more preferably by at least 50%, and most preferably, the function is inhibited by at least 75%. The terms "inhibit" and "block" are used interchangeably herein.

As used herein, the term "inhibitor" refers to a material, sample, or substance that retards or stops a chemical reaction (e.g. an enzymatic reaction).

As used herein, the term "iron deficiency anemia" refers to a decrease in the number of red cells in the blood caused by too little iron. Iron deficiency anemia is the most common form of anemia. Approximately 20% of women, 50% of pregnant women, and 3% of men are iron deficient. The causes of iron deficiency are too little iron in the diet, and poor absorption of iron by the body. It can also occur secondary to bleeding in patients with rheumatoid arthritis.

As used herein, the term "isocitrate" also includes isocitric acid. It is well known in the art that salts and esters of isocitric acid are known as isocitrate.

As used herein, the term "marker molecule" refers to a molecule, or aggregate of molecules, whose presence, absence and/or concentration in a sample is indicative of the presence or absence of a disease or other condition.

As used herein, the term "megakaryopoiesis" refers to the development of the bone marrow cells responsible for the production of blood platelets. Megakaryocytes are directly responsible for producing platelets which are needed for the formation of a thrombus, or blood clot. There are several diseases which are directly attributable to abnormal megakaryocyte function or abnormal platelet function, including thrombocythemia, which is a disorder characterized by high numbers of circulating platelets, and thrombocytopenia and megakaryocytopenia, which are characterized by low numbers of platelets and megakaryocytes, respectively.

As used herein, the term "metabolite" refers to the product of physiological processes involving one or several pharmaceutical agents, adjuvants, additives, or excipients used in formulation or combinations thereof.

As used herein, the term "neoplastic blood disorder" refers to the abnormal growth of red or white blood cells.

As used herein, the term. "oxalomalate" refers to the tricarboxylic acid (a-hydroxy-b-oxalosuccinic acid) formed in vitro and in vivo by condensation of oxaloacetate with glyoxylate.

The term "pharmaceutically acceptable carrier" refers to a non-toxic carrier, adjuvant, excipient, or vehicle that may be administered to a patient, together with a compound of this invention, and which does not destroy the pharmacological activity thereof. The term also encompasses any of the agents approved by a regulatory agency of the US Federal government or listed in the US Pharmacopeia for use in animals, including humans.

The terms "pharmaceutically acceptable salt" and "prodrug" are used throughout the specification to describe any pharmaceutically acceptable form (such as a salt, an ester, salt of an ester or a related group) of a compound which, upon administration to a patient, provides the compound described in the specification. In cases where compounds are sufficiently basic or acidic to form stable nontoxic acid or base salts, administration of the compounds as salts may be appropriate. The term pharmaceutically acceptable salts or complexes refers to salts or complexes that retain the desired biological activity of the compounds of the present invention and exhibit minimal undesired toxicological effects. Pharmaceutically acceptable salts may be obtained using standard procedures well known in the art, for example by reacting a sufficiently basic compound such as an amine with a suitable acid affording a physiologically acceptable anion. Lists of suitable salts can be found in, e.g., S. M. Birge et al., 1977, *J. Pharm. Sci.* 66: 1-19, herein incorporated by reference.

Specifically, the term "prodrug" as used herein refers to any compound that when administered to a biological system generates the drug substance, i.e. active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically-active compound. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

As used herein, the term "physiologically acceptable" ester or salt means an ester or salt form of the active ingredient which is compatible with any other ingredients of the pharmaceutical composition, which is not deleterious to the subject to which the composition is to be administered.

As used herein, the term "Do vera" refers to is an abnormal increase in blood cells (primarily red blood cells) resulting from excess production by the bone marrow.

As used herein, the terms "poly-nucleotide", "nucleotide sequence", "nucleic acid molecule", "nucleic acid" or "oligonucleotide" are used interchangeably and refer to a heteropolymer of nucleotides or the sequence of these nucleotides. These phrases also refer to DNA or RNA of genomic or synthetic origin which may be single-stranded or double-stranded and may represent the sense or the antisense strand. In the sequences herein, A is adenine, C is cytosine, G is guanine, T is thymine and N is G, A, C, T(U). It is contemplated that where the polynucleotide is RNA, the T (thymine) in the sequences provide herein may be substituted with U (uracil).

As used herein, the term "red blood cell" refers to a fully or partially differentiated erythrocyte, which may or may not have a micronucleus.

The term "standard," as used herein, refers to something used for comparison. For example, it can be a known standard agent or compound which is administered or added and used for comparing results when adding a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

As used herein, the term "succinate" is intended to mean the dicarboxylic acid $HOOCCH_2CH_2COOH$ that is formed in the Krebs cycle and in various fermentation processes. The term "succinate" as it is used herein is synonymous with the term "succinic acid." Chemically, succinate corresponds to a salt or ester of succinic acid. Therefore, succinate and succinic acid refer to the same compound, which can be present in either of the two forms depending on the pH of the solution.

As used herein, the term "thrombocytopenia" refers to a decreased platelet count in the blood relative to a normal platelet count. Such a decrease is meant herein to include any level below that determined as normal for the particular mammalian species of interest. Thrombocytopenia may appear at any stage of the mammal's development, and may be temporary or permanent. Where temporary, the disease may reappear at any time in the lifecycle of the mammal. Thrombocytopenia may or may not be inherited by the offspring of those mammals affected with it.

As used herein, a "subject in need thereof" is a patient, animal, mammal or human, who will benefit from the method of this invention. For example, this patient may be a person who has developed iron deficiency anemia, thrombocytopenia, or a neoplastic blood disorder such as polycythemia vera, or is believed to be at risk for developing iron deficiency anemia, thrombocytopenia, or a neoplastic blood disorder such as polycythemia vera.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

As used herein, a "therapeutic" treatment is a treatment administered to a subject who exhibits signs of pathology for the purpose of diminishing or eliminating those signs.

As used herein, a "therapeutically effective amount" of a compound is that amount of compound which is sufficient to provide a beneficial effect to the subject to which the compound is administered.

As used herein, "2-oxoglutarate" also refers to α-Ketoglutaric acid, α-ketoglutarate, 2-Ketoglutaric acid, and Oxoglutaric acid.

Whenever a term in the specification is identified as a range (i.e. C1-C12 alkyl), the range independently refers to each element of the range. As a non-limiting example, C1-C4 alkyl means, independently, $C_1$, $C_2$, $C_3$ or $C_4$ alkyl. Similarly, when one or more substituents are referred to as each independently being a group, this means that each substituent can be any element of that group, and any combination of these groups can be separated from the group. For example, if $R^1$ and $R^2$ are each independently X, Y, or Z, this separately includes the groups $R^1$ is X and $R^2$ is X; $R^1$ is X and $R^2$ is Y; $R^1$ is X and $R^2$ is Z; $R^1$ is Y and $R^2$ is X; $R^1$ is Y and $R^2$ is Y; $R^1$ is Y and $R^2$ is Z; $R^1$ is Z and $R^2$ is X; $R^1$ is Z and $R^2$ is Y; and $R^1$ is Z and $R^2$ is Z.

The term "alkyl" as used herein, unless otherwise specified, refers to a saturated straight, branched, or cyclic, primary, secondary, or tertiary hydrocarbon, including but not limited to groups with $C_1$ to $C_{12}$. Illustrative examples of alkyl groups are methyl, ethyl, propyl, isopropyl, cyclopropyl, butyl, secbutyl, isobutyl, tertbutyl, cyclobutyl, 1-methylbutyl, 1,1-dimethylpropyl, pentyl, cyclopentyl, isopentyl, neopentyl, cyclopentyl, hexyl, isohexyl, and cyclohexyl. Unless otherwise specified, the alkyl group can be unsubstituted or substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, thiol, imine, sulfonic acid, sulfate, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991.

The term "halo" or "halogen", as used herein, includes chloro, bromo, iodo, and fluoro.

The term "alkali metal cation", as used herein, refers to ion of alkali metal with a positive charge. The alkali metals are a series of elements comprising Group 1 of the periodic table: lithium (Li), sodium (Na), potassium (K), rubidium (Rb), caesium (Cs), and francium (Fr).

"Chromium" is a chemical element in the periodic table that has the symbol Cr and atomic number 24. Chromium (III) refers to trivalent chromium, also known as Cr(III) or $Cr^{3+}$.

Description of the Invention

This invention consists of an approach for the manipulation of red blood cell and platelet production either in vivo or ex vivo. The present invention encompasses the treatment of anemias that do not respond well to erythropoietin, such as anemia of chronic disease, also known as anemia of inflammation, anemia of renal failure, also known as anemia of chronic kidney disease and anemias in the elderly, often which are due to unknown causes. The present invention further encompasses treatment of polycythemia vera, a neoplastic blood disorder currently treated with either phlebotomy (blood drawing) or chemotherapy. The present invention also encompasses treatment of patients with low platelet counts after high dose chemotherapy to improve the recovery of the platelet counts. The present invention is also useful as a diagnostic tool to determine if red cell precursors sense iron deprivation.

The main treatment used to augment red cell production by the bone marrow is the growth factor erythropoietin, produced and marketed by Amgen (Thousand Oaks, Calif.). The latest version of erythropoietin being marketed by Amgen is a long acting variant called Aranesp (darbepoetin alfa). The compositions and methods of the present invention provide for the ability to augment the potency of erythropoietin in patients who otherwise respond poorly. The compositions and methods of the present invention also offer a substitute for erythropoietin in some patients, with the advantage that our compounds are cheaper and non-immunogenic.

The main small molecules now being developed to augment marrow production of red cells consist of HIF1α stabilizers, developed and entered into clinical trials by Fibrogen (San Francisco, Calif.). The main function of this compound is to augment the production of erythropoietin, and they will not be effective in patients whose anemias are refractory to erythropoietin.

The compositions and methods of the present invention provide a unique opportunity to use small-molecule compounds to manipulate red cell and platelet production in patients. No good treatments exist for anemias that fail to respond to erythropoietin. Such patients must either endure their anemia or receive blood transfusions which provide only transient benefit and have numerous risks and costs. The main small-molecule therapies being developed by other groups for treatment of anemia consist of a class of compounds which stabilize HIF1α, leading to enhanced erythropoietin production. However, these compounds are not likely to have efficacy in anemias associated with loss of responsiveness to erythropoietin. Thus, our approach opens a new therapeutic opportunity for the treatment of anemias unresponsive or poorly responsive to erythropoietin. The clinical need and the commercial market for such a treatment are enormous.

Accordingly, in one embodiment, this invention provides compositions comprising isocitrate for treating iron deficiency. In another embodiment, this invention provides derivatives of isocitrate for treating iron deficiency.

In one embodiment, the present application provides derivatives of isocitrate according to the formula (I):

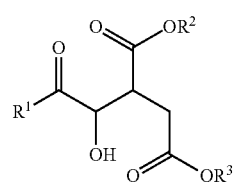

or a pharmaceutically acceptable salt or prodrug thereof, wherein $R^1$ is —$OR^4$, or —$NHCH_2C(O)OR^4$; $R^2$, $R^3$, and $R^4$ are each independently H, C1-C12 alkyl, or an alkali metal cation; or $R^2$, $R^3$, and $R^4$, taken together, is chromium (III) which forms chemical bonds with the oxygen atoms attached thereto; and with the following provisos that when $R^1$ is —$OR^4$, then at least one of $R^2$, $R^3$, and $R^4$ is neither H nor an alkali metal cation.

For example, the compound may be selected from the group consisting of:

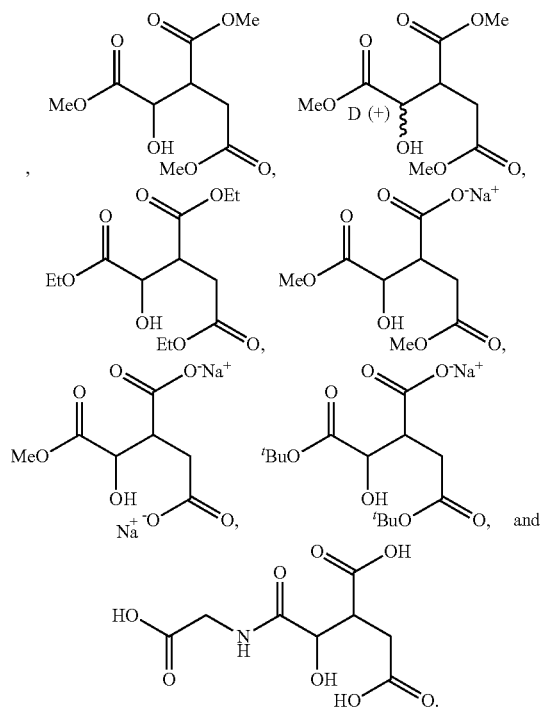

In another embodiment, the compound of formula (I) is represented by the formula (Ia):

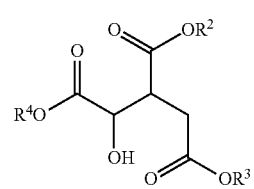

wherein, $R^2$, $R^3$, and $R^4$ are each independently H, C1-C12 alkyl, or an alkali metal cation; or $R^2$, $R^3$, and $R^4$, taken together, is chromium (III) which forms chemical bonds with the oxygen atoms attached thereto; and with the following provisos that at least one of $R^2$, $R^3$, and $R^4$ is neither H nor an alkali metal cation.

In another embodiment of the compound of the formula (Ia), $R^2$, $R^3$, and $R^4$ are the same or different, and are each independently C1-C12 alkyl.

In yet another embodiment of the compound of the formula (Ia), $R^3$ and $R^4$ each independently C1-C12 alkyl; and $R^2$ is H or an alkali metal cation.

In yet another embodiment of the compound of the formula (Ia), $R^4$ is C1-C12 alkyl; and $R^2$ and $R^3$ are each independently H or an alkali metal cation.

In another embodiment, the compound of formula (I) is represented by the formula (Ib):

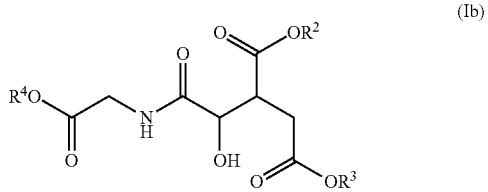

wherein $R^2$, $R^3$, and $R^4$ are each independently H, C1-C12 alkyl, or an alkali metal cation; or $R^2$, $R^3$, and $R^4$, taken together, is chromium (III) which forms chemical bonds with the oxygen atoms attached thereto.

In another embodiment of the compound of the formula (Ib), $R^2$, $R^3$, and $R^4$ are the same or different, and are each independently C1-C12 alkyl.

In yet another embodiment of the compound of the formula (Ib), $R^3$ and $R^4$ each independently H or an alkali metal cation.

In yet another embodiment of the compound of the formula (Ib), $R^4$ is C1-C12 alkyl; and $R^2$ and $R^3$ are each independently H or an alkali metal cation.

In another embodiment, isocitrate and isocitrate derivatives may be used to augment the activity of erythropoietin. Erythropoietin, also known as EPO, is a glycoprotein hormone that is produced by the body to regulate blood cell production and is produced mainly in the kidney of an adult and in the liver of a fetus. Thus, EPO is most often understood in terms of its effects on stimulating erythropoiesis. EPO is also an inducible cytokine which is produced in the brain in response to hypoxia. EPO protein and EPO receptor are expressed throughout the brain, including the mesencephalon, from development through adulthood. Synthetic and recombinant versions of EPO are also suitable for use in the present methods and compounds. In some embodiments, the EPO is human EPO, and preferably recombinant EPO, such as Epoetin alpha, distributed as PROCRIT™ by Ortho Biotech Products (Bridgewater, N.J.) or by Amgen as Epogen™. Various procedures for producing EPO are known and include those discussed in U.S. Pat. Nos. 5,955,422, 5,756,349, 5,621,080, 5,618,698, 5,547,933, 5,441,868 and 4,703,008, which are hereby incorporated by reference. In one embodiment the EPO is human EPO or human recombinant EPO.

In another embodiment, isocitrate and isocitrate derivatives may be used to stimulate the production of red blood cells. In yet another embodiment, isocitrate and isocitrate derivatives may be used to decrease megakaryopoiesis and the production of platelets. In yet another embodiment, isocitrate and isocitrate derivatives may be used to treat a subject with anemia.

In another embodiment, this invention provides compositions for decreasing red blood cell production comprising aconitase inhibitors. The conversion of citrate into cis-aconitate and isocitrate is mediated by the enzyme aconitase (Krebs, et al., 1952, J. Biochem 52(3): 527-528, herein incorporated by reference). Two aconitase enzymes, mitochondrial aconitase (mAcon) and cytosolic aconitase, are responsible for the conversion of the metabolic intermediate citrate into isocitrate. By preventing the conversion of citrate to isocitrate, an accumulation of citrate in the body occurs. We have shown that citrate enhances the block in erythroid differentiation, thus leading to reduced red blood cell production (see FIGS. 1D and 1H).

In one embodiment, this invention provides for the use of the aconitase inhibitor, oxalomalate, to decrease red blood cell production. Oxalomatate, a tricarboxylic acid (α-hydroxy-β-oxalosuccinic acid) is a known competitive inhibitor of aconitase (Ruffo, et al., 1962, Biochem J. 85: 588-93, herein incorporated by reference). Oxalomalate is formed in vitro and in vivo by condensation of oxaloacetate with glyoxylate.

In another embodiment, this invention provides for the use of the aconitase inhibitor, fluoroacetate, to decrease red blood cell production. Previous studies have shown that animals treated with fluoroacetate accumulate large quantities of citrate in their tissues (Buffa, et al., 1949, J. Physiol. 110: 480). This accumulation of citrate is caused by the inhibitory activity of fluoroacetate aconitase, which converts citrate to isocitrate.

In another embodiment, this invention provides for the use of an aconitase inhibitor to treat neoplastic blood disorders such as polycythemia vera and other myeloproliferative disorders. Examples of other myeloproliferative disorders include chronic myeloid leukemia (CML), essential thrombocythemia (ET), primary myelofibrosis (PMF), chronic neutrophilic (CNL), eosinophilic (CEL) and myelomonocytic (CMML) leukemias; juvenile myelomonocytic leukemia (JMML); hypereosinophilic syndrome (HES); systemic mastocytosis (SM); and others (Tefferi, et al., 2007, Cell Cycle 6(5): 550-66).

In another embodiment, this invention provides for the use of an aconitase inhibitor to treat thrombocytopenia, Thrombocytopenia is a condition in which the number of platelets per unit volume of peripheral blood is lower than normal. Specifically, thrombocytopenia refers to a decrease in the platelet count to 100,000/μL or lower compared to the normal platelet count, which generally ranges from 150,000 to 350,000/μL. Petechial bleeding and purpura are most frequently observed as initial symptoms, followed by nasal bleeding, gingival bleeding, and the like. Early diagnosis and early treatment are important also for the prevention of progress to more serious symptoms, such as cerebral bleeding. The following four factors (1) failed platelet production, (2) abnormal platelet distribution, (3) increased platelet destruction, and (4) increased platelet consumption are known as the mechanism of thrombocytopenia, however, its pathological features and causes vary widely. Specially, thrombocytopenia attributable to hepatic failure has been considered to be clinically problematic for a long time as one of the complications affecting patient prognosis. Some types of von Willebrand disease are rare diseases that exhibit thrombocytopenic symptoms and a bleeding tendency as a result of increased platelet consumption in the body due to congenital qualitative disorders of glycoprotein Ib and von Willebrand factor.

Conditions included in the scope of thrombocytopenia are the disease caused by radiation therapy and the disease accompanying bone marrow transplantation. Also included in the scope of thrombocytopenia are the disease caused by the selective suppression of megakaryocytes due, for example, to pharmaceutical drugs (phenylbutazone, gold compounds, tolbutamide and chemotherapeutics) and viral infection, the diseases caused by systemic myelocytic deficiencies such as aplastic anemia, autoimmune thrombocytopenic purpura, osteotmyelodysplasis syndrome, leukemia, multiple myeloma and megakaryoblastic anemia, drug-induced immune thrombocytopenia, post-transfusion purpura and secondary immune thrombocytopenia.

In another embodiment, this invention provides for the use of citrate or other Krebs cycle metabolite(s) or derivate(s) for decreasing red blood cell production. In a particular embodiment of this invention, the Krebs cycle metabolite or derivative is 2-oxoglutarate, succinate, or fumarate.

In another embodiment, this invention provides for the use of citrate or other Krebs cycle metabolite(s) or derivative(s) for treating a neoplastic blood disorder. In a particular embodiment of this invention, the neoplastic blood disorder is polycythemia vera.

In another embodiment, this invention provides for the use of citrate or other Krebs cycle metabolite(s) or derivative(s) for treating thrombocytopenia.

The present invention also provides methods of using pharmaceutical compositions of the inventive compounds. Such pharmaceutical compositions may be for administration for injection, or for oral, nasal, transdermal or other forms of administration, including, e.g., by intravenous, intradermal, intramuscular, intramammary, intraperitoneal, intrathecal, intraocular, retrobulbar, intrapulmonary (e.g., aerosolized drugs) or subcutaneous injection (including depot administration for long term release); by sublingual, anal, vaginal, or by surgical implantation, e.g., embedded under the splenic capsule, brain, or in the cornea. The treatment may consist of a single dose or a plurality of doses over a period of time. In general, comprehended by the invention are pharmaceutical compositions comprising effective amounts of a compound of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as potylactic acid, polyglycolic acid, etc. or into liposomes. Hyaluronic acid may also be used, and this may have the effect of promoting sustained duration in the circulation. The pharmaceutical compositions optionally may include still other pharmaceutically acceptable liquid, semisolid, or solid diluents that serve as pharmaceutical vehicles, excipients, or media, including but are not limited to, polyoxyethylene sorbitan monolaurate, magnesium stearate, methyl- and propylhydroxybenzoate, starches, sucrose, dextrose, gum acacia, calcium phosphate, mineral oil, cocoa butter, and oil of theobroma. Such compositions may influence the physical state, stability, rate of in vivo release, and rate of in vivo clearance of the present proteins and derivatives. See, e.g., *Remington's Pharmaceutical Sciences*, 18th Ed., 1990, Mack Publishing Co., Easton, Pa., pp. 1435-1712, which are herein incorporated by reference. The compositions may be prepared in liquid form, or may be in dried powder, such as lyophilized form. Implantable sustained release formulations are also contemplated, as are transdermal formulations.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys.

The invention also encompasses the use pharmaceutical compositions of an appropriate compound, homolog, fragment, analog, or derivative thereof to practice the methods of the invention, the composition comprising at least one appropriate compound, homolog, fragment, analog, or derivative thereof and a pharmaceutically-acceptable carrier.

The pharmaceutical compositions useful for practicing the invention may be administered to deliver an appropriate amount of the tracer molecule. Pharmaceutical compositions that are useful in the methods of the invention are generally administered locally, based on where the administration is and the tissue in which the visualization is to take place.

A pharmaceutical composition of the invention may be prepared, packaged, or sold in bulk, as a single unit dose, or as a plurality of single unit doses. As used herein, a "unit dose" s discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

The invention also includes a kit comprising a compound of the invention and an instructional material which describes administering the composition to a subject. In another embodiment, this kit comprises a (preferably sterile) solvent suitable for dissolving or suspending the composition of the invention prior to administering the compound to the subject.

In accordance with one aspect of the present invention, amounts of isocitrate and isocitrate derivatives effective to treat iron deficiency, stimulate the production of blood cells, and decrease megakaryopoiesis and platelet production are administered to the subject. Effective, but nontoxic amounts of isocitrate and isocitrate derivatives may be readily determined by the ordinary skilled physician. The precise amounts required for this purpose will depend upon the body weight of the patient, physiological condition of the patient, desired effect, and other factors. For example, at least about 10 mg of isocitrate or isocitrate derivative per kg of body weight of the subject may be administered per day, such as from about 100 to about 300 mg of isocitrate or isocitrate derivative per kg of body weight.

In accordance with another aspect of the invention, amounts of citrate or other Krebs cycle metabolites or derivatives effective to decrease red blood cell production, treat neoplastic blood disorders, and treat thrombocytopenia are administered to the subject. Effective, but nontoxic amounts of citrate or other Krebs cycle metabolites or derivatives may be readily determined by the ordinary skilled physician. The precise amounts required for this purpose will depend upon the body weight of the patient, physiological condition of the patient, desired effect, and other factors. For example, at least about 10 mg of citrate or other Krebs cycle metabolites or derivatives per kg of body weight of the subject may be administered per day, such as about 100 to about 300 mg of citrate or other Krebs cycle metabolites or derivatives per kg of body weight.

In accordance with yet another aspect of the invention, amounts of aconitase inhibitor effective to decrease red blood cell production, treat neoplastic blood disorders, and treat thrombocytopenia are administered to the subject. Effective, but nontoxic amounts of aconitase inhibitor may be readily determined by the ordinary skilled physician. The precise amounts required for this purpose will depend upon the body weight of the patient, physiological condition of the patient, desired effect, and other factors. For example, at least about 0.1 mg of aconitase inhibitor per kg of body weight of the subject may be administered per day, more preferably from about 1 to about 10 mg of aconitase inhibitor per kg of body weight.

In particular embodiments, the method may comprise administering the composition weekly, twice weekly, or even daily. It is further contemplated that treatment methods may involve multiple administrations daily. The method may comprise administering the compound daily such as by injection.

In another embodiment, the present invention is directed to a method of detecting iron deficiency comprising the steps of: (a) determining the concentration of at least one marker molecule selected from: (i) citrate; (ii) isocitrate; and (iii) a related metabolite in a body sample, and (b) comparing the level of the marker molecule within said body sample with the level of the marker molecule present in a healthy human body sample.

In yet another embodiment, the level of the marker molecule in a healthy human body sample is provided as a predetermined value to set up a threshold for the detection procedure.

In yet another embodiment, the level of the marker molecule in a healthy human body sample is determined from a standardized sample solution, or from a representative number of healthy human body samples.

In another embodiment, the present invention relates to a test kit for determination of iron deficiency in samples according to the method disclosed herein.

In accordance with one aspect of the invention, the concentrations of citrate and isocitrate can be determined using gas chromatography followed by mass spectrometry (Loe, et al., 2001, *Anal, Biochem.* 292(1): 148-54; Jensen, et al., 2006, *J. Biol. Chem,* 281: 22342-22351, which are herein incorporated by reference), by nuclear magnetic resonance (NMR) (Crockford, et al., 2005, *Anal, Chem,* 77(14): 4556-62, herein incorporated by reference), or by an enzyme based assay where the analyte serves as a metabolite for the generation of NADPH. (Petrarulo, et al., 1995, *Clin. Chem.* 41(10): 1518-21; Forni, et al., 2005, *Crit. Care* 9(5): R591-595, which are herein incorporated by reference).

In another embodiment, the present invention provides a nucleotide sequence encoding a polypeptide, HBLD2, that promotes the activity of aconitase. In a particular embodiment, the present invention provides a nucleic acid sequence according to SEQ ID NO: 1 or a fragment or homologue thereof.

Further, a homologous target polynucleotide sequence can be isolated by performing a polymerase chain reaction (PCR) using two degenerate oligonucleotide primer pools designed on the basis of amino acid sequences within the target polynucleotide of interest. The template for the reaction can be cDNA obtained by reverse transcription of mRNA prepared from the organism of interest. The PCR product can be subcloned and sequenced to ensure that the amplified sequences represent, the sequences of a homologous target polynucleotide sequence.

Alternatively, homologous target polynucleotides or polypeptides may be identified by searching a dataset to identify sequences having a desired level of homology to an essential polynucleotide of the invention. A variety of such databases are available to those skilled in the art including GenBank. In various embodiments, the databases are screened to identify nucleic acids with at least 97%, at least 95%, at least 90%, at least 85%, at least 80%, at least 70%, at least 60%, at least 50%, at least 40%, or at least 30% identity to an essential polynucleotide of the invention.

"Homologous sequences" or "homologues" as used herein are those sequences in which a first amino acid or nucleotide sequence contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity when optimally aligned. For example, amino acid or nucleotide sequences which share common structural domains have at least about 30-40% homology, preferably 40-50% homology, more preferably 50-60%, and even more preferably 60-70%, 70-80%, or 80-90% or 95% homology across the amino acid sequences of the domains and contain at least one and preferably two structural domains or motifs. Furthermore, amino acid or nucleotide sequences which share at least 30-40%, preferably 40-50%, more preferably 50-60%, 60-70%, 70-80%, or 80-90% or 95% homology and share a common functional activity are homologous.

In another embodiment, the present invention encompasses isolated nucleic acids comprising a nucleotide sequence that has at least 40%, 45%, 55%, 60%, 65%, 70%, 75%, 80%, 85%, 90%, 95%, 98% or more nucleotide sequence identity to the nucleotide sequence set forth in SEQ ID NO: 1. The nucleotide sequences of the invention also include nucleotide sequences that encode polypeptides having at least 25%, 30%, 40%, 50%, 55%, 60%, 65%, 70%, 75%, 80%, 85%, 90%, 95%, 98% or higher amino acid sequence identity or similarity to the amino acid sequence set forth in SEQ ID NO: 2.

In another embodiment, the present invention provides a polypeptide corresponding to SEQ ID NO: 2 or a fragment or derivative thereof. The polypeptide of the invention used and encompassed in the methods and compositions of the present invention include the polypeptide encoded by the polynucleotide sequence of SEQ ID NO: 11 as described above.

As used herein, the term "polypeptide" refers to any peptide or protein including two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. "Polypeptides" may contain amino acids other than the 20 gene-encoded amino acids. Polypeptides" include amino acid sequences modified either by natural processes, such as post-translational processing, or by chemical modification techniques which are well-known in the art. Such modifications are well described in basic texts and in more detailed monographs, as well as in research literature.

Modifications can occur anywhere in a polypeptide, including the peptide backbone, the amino acid side-chains and the amino or carboxyl termini. A given polypeptide may contain many types of modifications. Polypeptides may be branched, or cyclic, with or without branching. Cyclic, branched and branched-cyclic polypeptides may result from posttranslational natural processes or may be made by synthetic methods. Modifications include but are not limited to acetylation, acylations, amidation, covalent attachment of flavin, disulfide bond formation, formation of covalent cross-links, and glycosylation. See, for instance, Proteins—structure and molecular properties, $2^{nd}$ Ed., T. E. Creighton, W.H. Freeman and Company, New York (1993); F. Wold, Posttranslational protein modifications: perspectives and prospects, pgs 12 in Posttranslational covalent modification of proteins, B. C. Johnson, Ed., Academic Press, New York (1983); S. Seifter and S. Englard, Analysis for protein modifications and nonprotein cofactors, 182 Methods of Enzymology 626 (1990); and S. I. Rattan et al., Protein synthesis, posttranslational modifications, and aging, 663 Ann NY Acad Sci 48 (1992).

In a another embodiment, the present invention relates to the use of the polypeptide of SEQ NO: 2 or an agonist thereof to treat iron deficiency.

In another embodiment, the polypeptide sequence according to SEQ ID NO: 2 or an agonist thereof may be used to augment the activity of erythropoietin.

In another embodiment, the polypeptide sequence according to SEQ ID NO: 2 or an agonist thereof may be used to stimulate the production of red blood cells. In yet another embodiment, the polypeptide sequence according to SEQ ID NO: 2 or an agonist thereof may be used to decrease megakaryopoiesis and the production of platelets. In yet another embodiment, the polypeptide sequence according to SEQ ID NO: 2 or an agonist thereof may be used to treat a subject with anemia.

The peptides of the present invention may be readily prepared by standard, well-established techniques, such as solid-phase peptide synthesis (SPPS) as described by Stewart et al. in Solid Phase Peptide Synthesis, 2nd Edition, 1984, Pierce Chemical Company, Rockford, Ill.; and as described by Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenyl esters.

Examples of solid phase peptide synthesis methods include the BOC method which utilized tert-butyloxcarbonyl as the α-amino protecting group, and the FMOC method which utilizes 9-fluorenylmethyloxcarbonyl to protect the α-amino of the amino acid residues, both methods of which are well known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane, Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl-blocking group at the N-terminus, tier instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high-resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide. Prior to its use, the peptide is purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as C4-, C8- or C18-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

It will be appreciated, of course, that the peptides or antibodies, derivatives, or fragments thereof may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

The present invention also provides for homologs of proteins and peptides. Homologs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. To that end, 10 or more conservative amino acid changes typically have no effect on peptide function.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides or antibody fragments which have been modified using ordinary molecular biological techniques so as to improve their resistance to proteolytic degradation or to optimize solubility properties or to render them more suitable as a therapeutic agent. Homologs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego, herein incorporated by reference).

It is not intended that the present invention be limited by the nature of the nucleic acid employed. The target nucleic acid may be native or synthesized nucleic acid. The nucleic acid may be from a viral, bacterial, animal or plant source. The nucleic acid may be DNA or RNA and may exist in a double-stranded, single-stranded or partially double-stranded form. Furthermore, the nucleic acid may be found as part of a virus or other macromolecule. See, e.g., Fasbender et al., 1996, *J. Biol. Chem.* 272:6479-89, herein incorporated by reference.

Nucleic acids useful in the present invention include, by way of example and not oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, *Oligonucleotide Synthesis, a Practical Approach*, IRL Press, Oxford, England, herein incorporated by reference). RNAs may be produce in high yield via in vitro transcription using plasmids such as SP65 (Promega Corporation, Madison, Wis.).

In some circumstances, as where increased nuclease stability is desired, nucleic acids having modified internucleoside linkages may be preferred. Nucleic acids containing modified internucleoside linkages may also be synthesized using reagents and methods that are well known in the art. For example, methods for synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide (—CH2-S—CH2), diinethylene-sulfoxide (—CH2-SO—CH2), dimethylene-sulfone (—CH2-SO2-CH2), 2'-O-alkyl, and 2'-deoxy2'-fluoro phosphorothioate internucleoside linkages are well known in the art (see Uhlmann et al., 1990, *Chem. Rev.* 90:543-584; Schneider et al., 1990, *Tetrahedron Lett.* 31:335 and references cited therein).

The nucleic acids may be purified by any suitable means, as are well known in the art. For example, the nucleic acids can be purified by reverse phase or ion exchange HPLC, size exclusion chromatography or gel electrophoresis. Of course, the skilled artisan will recognize that the method of purification will depend in part on the size of the DNA to be purified.

The term nucleic acid also specifically includes nucleic acids composed of bases other than the five biologically occurring bases (adenine, guanine, thymine, cytosine and uracil).

The present invention is directed to useful aptamers. In one embodiment, an aptamer is a compound that is selected in vitro to bind preferentially to another compound (in this case the identified proteins). In one aspect, aptamers are nucleic acids or peptides, because random sequences can be readily generated from nucleotides or amino acids (both naturally occurring or synthetically made) in large numbers but of course they need not be limited to these. In another aspect, the nucleic acid aptamers are short strands of DNA that bind protein targets. In one aspect, the aptamers are oligonucleotide aptamers. Oligonucleotide aptamers are oligonucleotides which can bind to a specific protein sequence of interest. A general method of identifying aptamers is to start with partially degenerate oligonucleotides, and then simultaneously screen the many thousands of oligonucleotides for the ability to bind to a desired protein. The bound oligonucleotide can be eluted from the protein and sequenced to identify the specific recognition sequence. [For example, see the following publications describing in vitro selection of aptamers: Klug et al., 1994, *Mol. Biol. Reports* 20: 97-107; Wallis, et al., *Chem. Biol.* 2:543-552 (1995); Ellington et al., 1994, *Curr. Biol.* 4:427-429; Lato et al., 1995, *Chem. Biol.* 2:291-303 (1995); Conrad et al., 1995, *Mol. Div.* 1:69-78; and Uphoff et al., 1996, *Curr. Opin. Struct. Biol.* 6:281-287.]

One of ordinary skill in the art will readily appreciate that the present invention is well adapted to carry out the objects and obtain the ends and advantages mentioned, as well as those inherent therein. The present invention may be embodied in other specific forms without departing from the spirit or essential attributes thereof.

Some examples of diseases and disorders which may be treated according to the methods of the invention are discussed herein. The invention should not be construed as being limited solely to these examples.

The following examples are intended to illustrate, but in no way limit the scope of the invention.

EXAMPLE 1

For each of the examples described herein, cell cultures were handled similarly. In particular, primary human CD34+ hematopoietic progenitor cells obtained from the National Heart Lung and Blood Core Facility at the Fred Hutchinson Cancer Research Center were cultured in serum free medium (SFM: Iscove's Modified Dulbecco's Medium (IMDM) supplemented with lot tested BSA, insulin, transferrin, selenium, and β-ME) with growth factors and iron added as indicated below. The cells were initially thawed from frozen vials and subjected to 48 hours of culture in pre-stimulation medium which consists of SFM with 100% iron saturated transferrin (80 ng/ml total iron in medium) and the following hematopoietic cytokines: 100 ng/ml SCF (stem cell factor), 100 ng/ml (FLT3-Ligand), 100 ng/ml TPO (thrombopoietin), and 50 ng/ml IL-3. After the 48 hour pre-stimulation phase, the cells were shifted to erythroid medium consisting of SFM with 3 U/ml Epo (erythropoietin) and 25 ng/ml SCF. The high iron erythroid cultures, indicated in the Figures as "100%", contain 100% iron saturated transferrin (79.8 ng/ml total iron), and the iron deprived erythroid cultures, indicated in the Figures as "15%"; contain 15% iron saturated transferrin (12.9 ng/ml total iron). Where indicated, cultures were supplemented with sodium isocitrate or sodium citrate.

In this experiment, cells were cultured in erythroid medium in high iron (100%) or iron deprived (15%) conditions. Where indicated, the cultures were supplemented with 20 mM isocitrate (Iso) or 20 mM citrate (Cit). After 5 days of culture, the cells were harvested for flow cytometric analysis to determine surface expression of the red cell marker glycophorin A (GPA) or of the megakaryocytic marker CD41. The analyses were carried out using a Becton Dickinson FacsCalibur flow cytometer and the FloJo (Treestar) software package. The same cells were analyzed for death. The cells harvested after 5 days of culture were stained with FITC-Annexin V, which marks apoptotic cells, and 7-AAD, which marks all dead cells. Cells which mark only with FITC-Annexin V are true apoptotic cells.

As shown in FIG. 1A, when we culture primary human hematopoietic progenitor cells, purified CD34+ cells, from the peripheral blood of normal donors treated with G-CSF (granulocyte colony stimulating factor) in medium with Epo, SCF and 100% transferrin saturation, the cells undergo erythroid differentiation as indicated by upregulation of the red cell surface protein glycophorin A (GPA). When we limit the iron levels in these cultures to approximate conditions of human iron deficiency anemia, 15% transferrin saturation, the progenitor cells manifest a block in erythroid differentiation, characterized by fewer GPA+ cells and lower levels of GPA on the positive cells (FIG. 1B). In addition, these iron deprived cultures show an abnormal outgrowth of megakaryocytic precursors, characterized by CD41 expression (FIG. 1B). This latter finding correlates with the increased platelet counts seen in cases of human iron deficiency anemia. Provision of 20 mM sodium isocitrate in the iron deprived cultures completely reverses the block in erythroid differentiation and eliminates the abnormal outgrowth of megakaryocytic precursors (FIG. 1C).

In addition, isocitrate supplementation completely reverses the increase in cell death seen in the iron deprived cultures, reflected by the staining of cells with the indicator dyes 7-AAD and FITC-Annexin V (FIGS. 1E-G). As a control, parallel cultures supplemented with 20 mM citrate showed enhancement of the block in erythroid differentiation and increased cell death, despite the highly similar molecular structures of citrate and isocitrate (FIGS. 1D, H).

EXAMPLE 2

Figure 2:
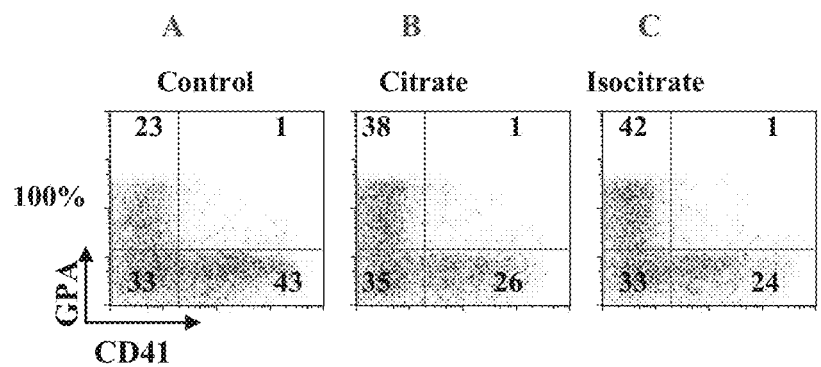
FIG. 2. Both isocitrate and citrate enhance erythroid differentiation in high iron conditions. A-C. Experiments were carried out as in FIG. 1 except that only high iron conditions were used. Citrate was added at 10 mM, and isocitrate was added at 20 mM.

We found that supplementation of cultures with 20 mM isocitrate also enhanced erythroid differentiation in cultures with adequate levels of iron consisting of 100% transferrin saturation, "iron replete cultures" (FIGS. 2A, C). Interestingly, providing 10 mM citrate in iron replete cultures also enhanced erythroid differentiation, most likely due to functional aconitase enzymes converting the citrate to isocitrate (FIG. 2B). We have performed additional experiments to ensure that the effects observed are not simply on GPA expression but rather reflect global erythroid differentiation.

EXAMPLE 3

In this experiment, we found that isocitrate enhances the hemoglobinization of human CD34+ cells in erythroid cultures. Briefly, cells were cultured 5 days in erythroid medium under the indicated conditions. Isocitrate was included, where indicated, at 20 mM. Culture samples were centrifuged in microcentrifuge tubes, and cell pellets were photographed against a white background. The sizes of the cell pellets reflect the numbers of cells present in the various samples, and the redness (i.e. darkness) of the pellets indicates the degree of hemoglobinization of the cells.

Figure 3:
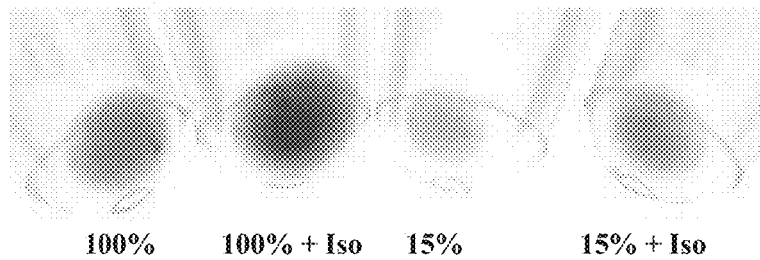
FIG. 3. Isocitrate enhances the hemoglobinization of human CD34+ cells in erythroid cultures. Cells were cultured 5 days in erythroid medium under the indicated conditions. Isocitrate was included, where indicated, at 20 mM. Culture samples were centrifuged in microcentrifuge tubes, and cell pellets were photographed against a white background. The sizes of the cell pellets reflect the numbers of cells present in the various samples, and the redness (i.e. darkness) of the pellets indicates the degree of hemoglobinization of the cells.

FIG. 3 shows a simple assay in which erythroid cultures −/+ iron deprivation and −/+20 mM isocitrate were analyzed for hemoglobin production by visual inspection of cell pellets for red pigmentation. As illustrated in FIG. 3, iron deprivation as expected impaired the hemoglobinization of the cells. Notably, treatment of cells with 20 mM isocitrate reversed the block in hemoglobinization caused by iron deprivation. Even more strikingly, 2.0 mM isocitrate substantially enhanced hemoglobinization of cells under iron replete conditions (FIG. 3).

Figure 4:
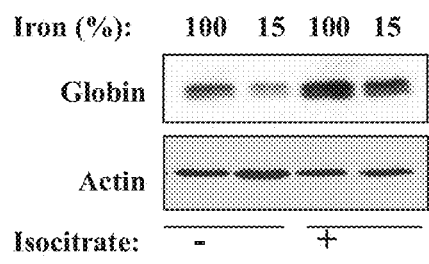
FIG. 4. Isocitrate enhances the globin chain synthesis of human CD34+ cells in erythroid cultures. Cells were cultured 5 days in erythroid medium under the indicated conditions. Isocitrate was included, where indicated, at 2.0 mM. Culture samples were harvested for Western blot analysis to detect expression of the α-globin protein using a rabbit anti-HbA (AXL 241 from Accurate Chemical and Scientific). The same membrane was also analyzed for levels of actin as a lane loading control.

These results were confirmed at a molecular level by immunoblotting for alpha globin protein (FIG. 4). Thus, our data show that isocitrate substantially augments the programming of red cell differentiation by erythropoietin acting on primary human hematopoietic progenitor cells and can override the inhibitory effects of iron deficiency.

Figure 5:
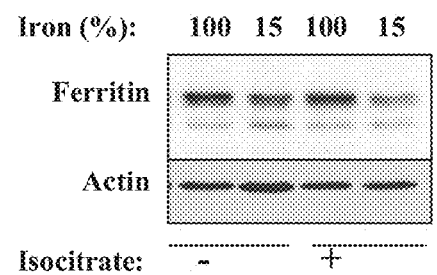
FIG. 5. Isocitrate does not affect intracellular iron stores. Western blot analysis was conducted as in FIG. 4 using an antibody to ferritin heavy chain. The levels of ferritin heavy chain within the cells rise or fall in direct proportion to the intracellular free iron levels. Note that inclusion of 20 mM isocitrate in the iron deprived cultures does not prevent to drop in ferritin heavy chain expression.

We performed several control experiments to prove that these effects of isocitrate are not due to the contamination of the preparation by iron. Firstly, we have performed mass spectrometry on the sodium isocitrate solution (DL-Isocitric Acid Trisodium salt, purchased from MP Biomedicals, LLC) and have found no contaminating iron, with an assay sensitivity of 5 ppm. Secondly, we have shown that there is no change in intracellular iron stores as a consequence of isocitrate treatment. In particular, we have subjected erythroid cultures −/+ iron deprivation and −/+20 mM isocitrate to immunoblot analysis for ferritin heavy chain, an intracellular protein whose levels drop with iron deprivation and increase with iron supplementation. As shown in FIG. 5, supplementation of cultures with 20 mM isocitrate had no effect on cellular ferritin heavy chain levels.

EXAMPLE 4

In this experiment, we compared the ability of isocitrate to reverse the effects of iron deprivation with that of competing technology. Fibrogen has developed compounds for treatment of anemia that act through the stabilization of hypoxia-inducible factor (HIF). One of these compounds, FG 4497, was obtained from Fibrogen and tested in a model of in vitro erythropoiesis. It was found that FG 4497 at 20 µM and 50 µM (doses recommended by company) showed no ability to reverse the effects of iron deprivation. Therefore, the data demonstrate that our compound isocitrate acts through a mechanism distinct from HIF stabilization and shows efficacy in circumstances where HIF stabilizers have proven completely ineffective.

EXAMPLE 5

In this experiment, we identified a gene which can protect red cell precursors from the effects of iron deprivation. As shown above, isocitrate reverses the effects of iron deficiency. The conversion of citrate to isocitrate is mediated by the enzyme aconitase (Krebs, et at, 1952, *J. Biochem* 52(3): 527-528). The two aconitase enzymes, mitochondrial aconitase (mAcon) and cytosolic aconitase, are responsible for the conversion of the metabolic intermediate citrate into isocitrate. To further characterize the role of the aconitase enzymes, we investigated the influence of a gene HBLD2 (HESB-like domain containing protein 2), which promotes the function of aconitase. Human CD34+ cells were transduced with either parent vector (MIG) or constructs encoding the Fe—S cluster assembly factors HBLD2, HBLD1, or HBLD1 variant R51C. The HBLD2 accession number in the NCBI nucleotide database is BC071621. The IMAGE clone ID number is 5107151, which corresponds to the catalog number for the plasmid containing the cDNA ordered from Open Biosystems. The cells underwent 5 days of erythroid culture in media with either 100% or 15% transferrin saturation and were analyzed by FACS.

Figure 6:
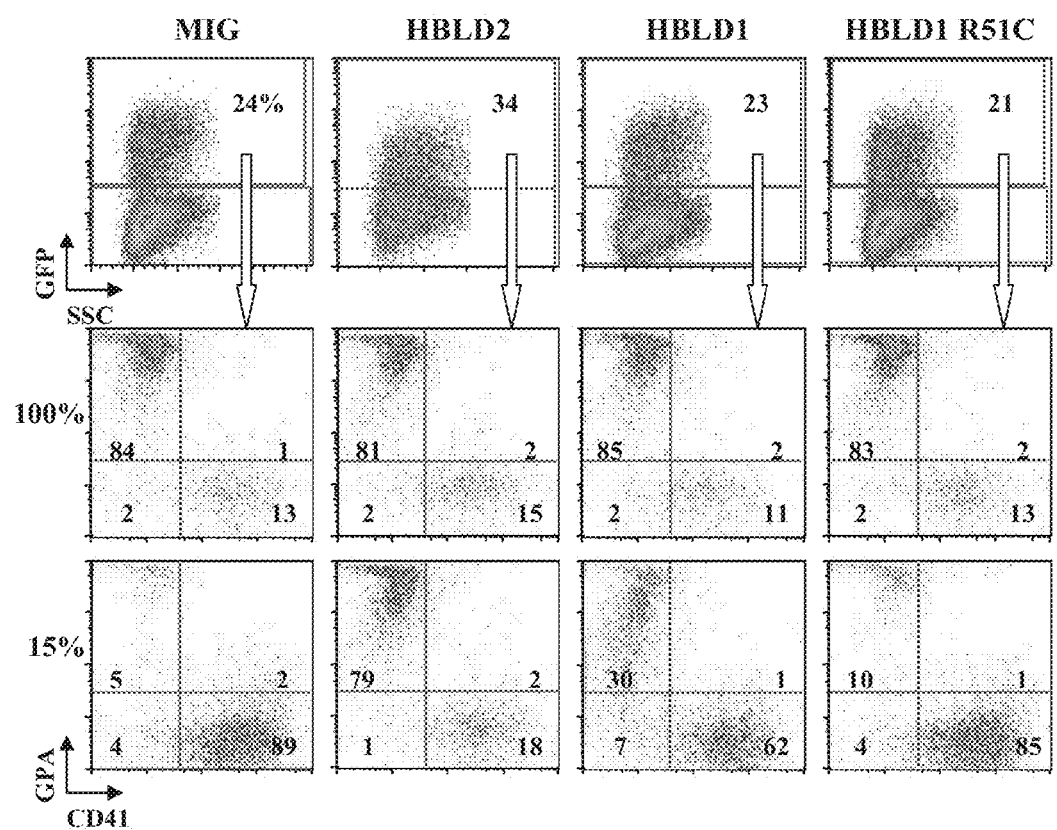
FIG. 6. Complete reversal of the erythroid iron deprivation response by the human ISCA homolog HBLD2. A related factor HBLD1 shows only minor reversal. Human CD34+ cells were transduced with either parent vector (MIG) or constructs encoding the Fe—S cluster assembly factors HBLD2, HBLD1, or HBLD1 variant R51C. The cells underwent 5 days of erythroid culture in media with either 100% or 15% transferrin saturation and were analyzed by FACS.

As shown in FIG. 6, introduction of the HBLD2 gene into human progenitor cells protected them from the effects of iron deficiency, further confirming a role for isocitrate in this process. A related factor HBLD1 (HESB-like domain containing protein 1), and its variant HBLD1. R51C, showed only minor reversal.

The experiment shown in FIG. 6 demonstrates that expression of a protein that drives aconitase activity causes efficient red cell development to occur even in the face of iron deprivation. This experiment provides further biologic evidence on the basic importance of isocitrate in programming red cell development. Furthermore, we have discovered that the aconitase enzymes are critical regulators of the differentiation of red cell precursors in the bone marrow. Moreover, these experiments demonstrate that the aconitase enzymes depend upon iron for their function and are compromised under conditions of iron deficiency.

EXAMPLE 6

In these experiments, the maximal tolerated dosage of isocitrate was examined in a mouse model. 5-6 week old C57BL/6 mice received once daily intraperitoneal injections of control saline or isocitrate solution at 100, 200, and 400 mg/kg. Three mice in each group received this treatment for 5 consecutive days, and on day 6 the mice were subjected to analysis of blood counts and marrow cells. This treatment was extremely well tolerated with no evidence of any toxicity even at the highest dose. Table 1 shows that the mice receiving the 200 mg/kg dose displayed a statistically significant increase in hemoglobin (Hb) and mean corpuscular hemoglobin concentration (MCHC).

TABLE 1

Effects of Isocitrate on Hemoglobin Production in Mice

| Treatment | RBC (10⁶ cells/μl) | Platelets (10³/μl) | HCT (%) | Hb (g/dL) | MCV (fl) | MCHC (g/dL) | RDW (%) |
|---|---|---|---|---|---|---|---|
| Saline | 7.97 ± 1.44 | 2563 ± 450 | 33.5 ± 6.0 | 12.7 ± 1.6 | 42.0 ± 0.4 | 38.1 ± 2.1 | 17.6 ± 0.2 |
| 100 mg/kg | 8.47 ± 1.15 | 2681 ± 369 | 35.7 ± 5.3 | 13.9 ± 1.8 | 42.1 ± 0.5 | 39.0 ± 1.5 | 18.8 ± 1.5 |
| 200 mg/kg | 8.47 ± 0.26 | 2608 ± 175 | 36.0 ± 1.4 | 14.8 ± 0.6* | 42.4 ± 0.5 | 41.2 ± 0.1# | 17.8 ± 0.9 |

Data represent mean plus or minus standard deviation.
p values were calculated using Student's t-test.
*p = 0.046
p = 0.032

These results correlate with FIG. 3, in which isocitrate increased the hemoglobin expression in human red cell precursors in culture.

In additional experiments, we have further increased the doses of isocitrate up to 800 mg/kg/day for 5 days and still have seen no evidence of toxicity in the mice. In this latter experiment we were unable to obtain blood values due to malfunctioning of the analyzer. However, flow cytometry on the marrows of mice receiving isocitrate suggested an enhancement of erythropoiesis.

EXAMPLE 7

Figure 7:
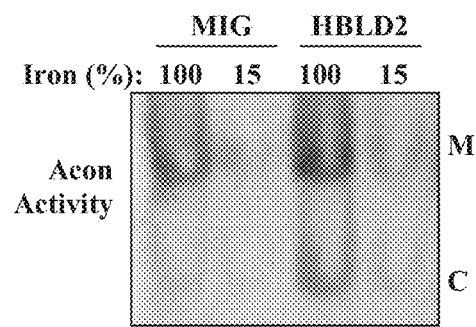
FIG. 7. HBLD2 regulates aconitase activity. Human CD34+ cells were transduced with parent vector (MIG) or with an expression vector for HBLD2 Cells were cultured 4 days in erythroid medium with either 100% or 15% saturated transferrin. Triton X-100 cellular extracts were subjected to in gel aconitase activity assays as described by Tong and Rouault (Cell Metabolism 3:199, 2006). Positions of mitochondrial (M) and cytosolic (C) isoforms are indicated.

In these experiments, we investigated the biochemical consequences of enforced HBLD2 expression in human primary erythroid cells. As shown above in FIG. 6, we found that retroviral transduction of HBLD2 could rescue erythroid progenitors from the inhibitory effects of iron deprivation. To address the biochemical consequences of enforced HBLD2 expression, transduced human CD34⁺ hematopoietic progenitor cells underwent assays for aconitase activity. The results in FIG. 7 show upregulation of both mitochondrial and cytosolic aconitase activities in response to HBLD2 expression. However, even in cells overexpressing HBLD2, the aconitase activities were downregulated as a consequence of iron deprivation. These results suggest increased HBLD2 levels do not eliminate the responsiveness of aconitases to iron deprivation but do raise the set points of the enzymes above a critical threshold, preventing triggering of the erythroid iron deprivation response.

Figure 8:
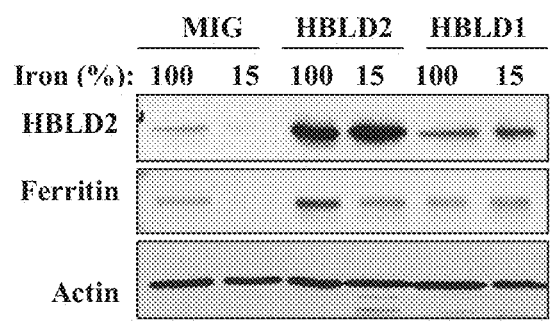
FIG. 8. HBLD2 regulates and is regulated by intracellular iron levels. Human CD34+ cells were transduced with parent vector (MIG) or with expression vectors for HBLD2 and HBLD1. Cells were cultured 4 days in erythroid medium with either 100% or 15% saturated transferrin. Whole cell lysates underwent immunoblotting with antibodies to HBLD2, ferritin heavy chain, a marker of intracellular iron stores, and to actin.

To determine the effects of HBLD2 levels on intracellular iron stores, transduced cells were assessed for expression of ferritin heavy chain. Increased iron incorporation into iron-sulfur clusters prevents IRP1 from binding to the Ferritin IRE and thereby promotes increased ferritin protein levels through enhanced translation. As shown in FIG. 8, HBLD2 overexpression led to increased ferritin levels, compatible with increased incorporation of iron into iron-sulfur clusters. As with the aconitase assays, iron deprivation diminished ferritin levels even in the cells overexpressing HBLD2, again consistent with a role for HBLD2 in establishing set points for iron-sulfur cluster assembly but not affecting responsiveness to iron deprivation. By contrast, HBLD1 overexpression did not increase ferritin levels under iron repletion but did blunt responsiveness to iron deprivation. Analysis of HBLD2 expression showed downregulation of the endogenous protein under iron deprivation, in parallel with ferritin levels, but no changes in the exogenously expressed protein. These results suggest that HBLD2 is regulated by iron at a translational or transcriptional level.

EXAMPLE 8

Figure 9:
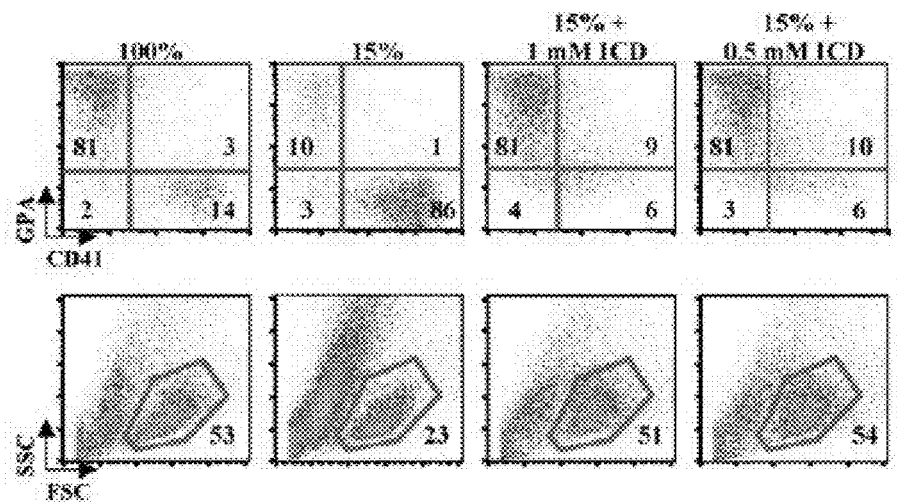
FIG. 9. Complete reversal of the erythroid iron deprivation response by the methyl ester of isocitrate (MIC). Human CD34$^+$ cells underwent 5 days culture in erythroid medium with 100% or 15% transferrin saturation followed by FACS analysis. Where indicated, cultures were supplemented with 1 mM or 0.5 mM methyl isocitrate (MIC). For analysis of the erythroid and megakaryocytic markers, GPA and CD41, gating was on live cells, as shown in bottom panels.
Figure 10:
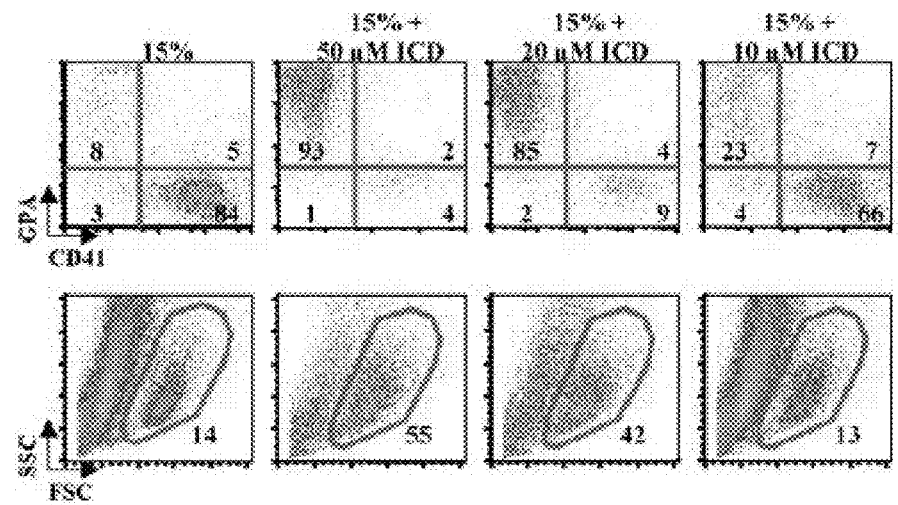
FIG. 10. Reversal of the erythroid iron deprivation response by low doses of the methyl ester of isocitrate (MIC). Human CD34$^+$ cells underwent 5 days culture in erythroid medium with 15% transferrin saturation followed by FACS analysis. Where indicated, cultures were supplemented with 50 μM, 20 μM and 10 μM methyl isocitrate (MIC). For analysis of GPA and CD41, gating was on live cells, as shown in bottom panels.

To optimize the in vivo efficacy of isocitrate, esterified versions have been synthesized. Previously, we found that high levels of trisodium citrate salt (20 mM) were required to rescue erythroid differentiation under conditions of iron deprivation. Initial experiments testing ethyl ester and lactone derivatives showed no rescue of erythroid differentiation (data not shown). By contrast, our first experiment with the methyl ester of isocitrate (MIC) showed complete rescue of erythroid differentiation at doses down to 0.5 mM (FIG. 9). Further titration demonstrated virtually complete rescue by MIC down to 20 μM and partial rescue with as little as 10 μM (FIG. 10). These results confirm the feasibility of synthesizing potent, pharmacologically active variants of isocitrate. The high in vitro efficacy of MIC at 20 μM suggests the engagement of a signaling pathway rather than a metabolic replacement effect.

EXAMPLE 9

Figure 11:
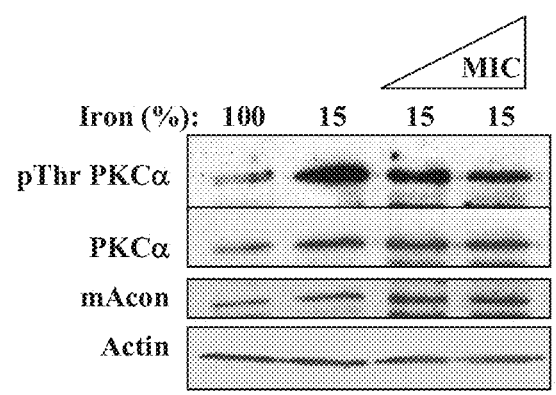
FIG. 11. Iron deprivation induces activation of protein kinase C α (PKCα), an effect partially reversed by isocitrate. Human CD34$^+$ cells were cultured 4 days in erythroid medium with either 100% or 15% saturated transferrin. Cells were also treated with either 0.5 or 1.0 mM methyl isocitrate (MIC) as indicated. Whole cell lysates underwent immunoblotting with the indicated antibodies.

We have also focused on the iron-responsive signaling pathways that are modulated by exogenous isocitrate. Preliminary experiments have addressed a potential role for protein kinase C (PKCα), due to its specialized role in erythropoietin signaling (Myklebust et al., Blood 95:510-518, 2000) and due to the regulatory interaction between PKC and cytosolic aconitase (Pitula et al., PNAS 101:10907-11, 2004). Expression levels and activation status of PKCα were assessed in primary human erythroid cells under various conditions (FIG. 11). Notably, iron deprivation strongly augmented PKCα autophosphorylation on T638 within the catalytic domain. Treatment with methyl isocitrate partially reversed the activation of PKCα by iron deprivation. These results thus raise the possibility that PKC may signal to aconitase, downstream of iron, and may also respond to isocitrate.

EXAMPLE 10

Preparation of the Isocitrate Derivatives of Formula (I)

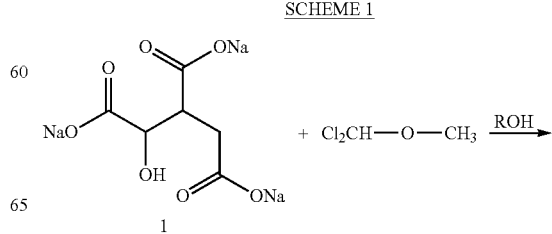

SCHEME 1

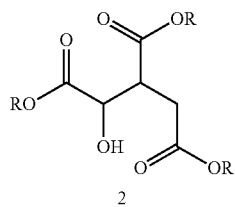

R = Me, Et, or tBu.

In one embodiment of the present invention, the tri-ester derivatives of isocitrate (2) were prepared from tri-sodium isocitrate (1) and dichloro(methoxy)methane as shown in Scheme 1. More specifically, compound 1 (1 equivalent) and dichloro(methoxy)methane (about 10 equivalent) were sequentially added to ROH in a flask at 0° C. The resulting mixture was stirred at 0° C. for about 30 minutes, then slowly warmed to the room temperature. The reaction mixture was then stirred at room temperature for about 24 hours. The solvent was removed under vacuum and then the crude product was purified through chromatograph. This afforded compound 2 with a yield of about 65 to 80%.

SCHEME 2

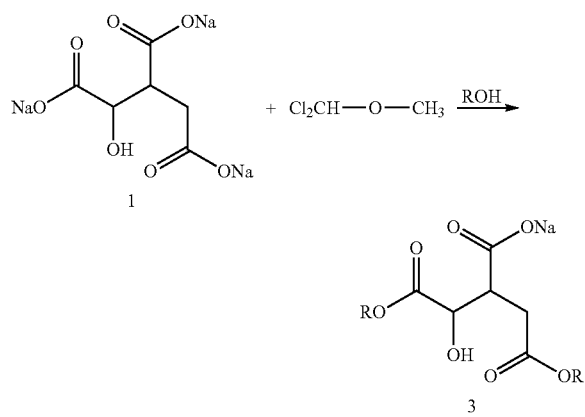

R = Me, Et, or tBu.

In one embodiment of the present invention, the bis-ester derivatives of isocitrate (3) were prepared from tri-sodium isocitrate (1) and dichloro(methoxy)methane as shown in Scheme 2. More specifically, compound 1 (1 equivalent) and dichloro(methoxy)methane (about 2 to 3 equivalent) were sequentially added to ROH in a flask at 0° C. The resulting mixture was stirred at 0° C. for about 30 minutes, then slowly warmed to the room temperature. The reaction mixture was then stirred at room temperature for about 24 hours. The solvent was removed under vacuum and then the crude product was purified through chromatograph. This afforded compound 2 with a yield of about 50 to 60%.

SCHEME 3

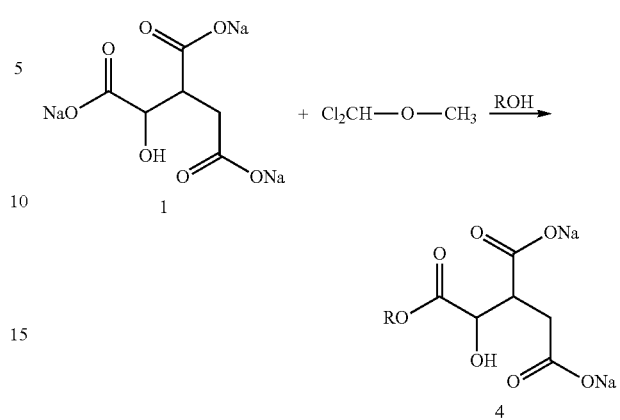

R = Me, Et, or tBu.

In one embodiment of the present invention, the mono-ester derivatives of isocitrate (4) were prepared from tri-sodium isocitrate (1) and dichloro(methoxy)methane as shown in Scheme 3. More specifically, compound 1 (1 equivalent) and dichloro(methoxy)methane (about 1 equivalent) were sequentially added to ROH in a flask at 0° C. The resulting mixture was stirred at 0° C. for about 30 minutes, then slowly warmed to the room temperature. The reaction mixture was then stirred at room temperature for about 24 hours. The solvent was removed under vacuum and then the crude product was purified through chromatograph. This afforded compound 2 with a yield of about 30 to 50%.

It should be understood to one skilled in the art that the above procedures are described as exemplary examples, and the compounds of the present invention can also be prepared through other synthetic methods known in the art.

The disclosures of each and every patent, patent application, and publication cited herein are hereby incorporated by reference herein in their entirety. One of skill in the art will appreciate that the superiority of the compositions and methods of the invention relative to the compositions and methods of the prior art are unrelated to the physiological accuracy of the theory explaining the superior results.

Headings are included herein for reference and to aid in locating certain sections. These headings are not intended to limit the scope of the concepts described therein under, and these concepts may have applicability in other sections throughout the entire specification.

Other methods which were used but not described herein are well known and within the competence of one of ordinary skill in the art of clinical, chemical, cellular, histochemical, biochemical, molecular biology, microbiology and recombinant DNA techniques.

The description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Accordingly, the present invention is not intended to be limited to the embodiments shown herein but is to be accorded the widest scope consistent with the principles and novel features disclosed herein.

We claim:

1. A method of treating iron deficiency comprising administering to a subject in need thereof a composition free of iron contamination, wherein said composition comprises a therapeutically effective amount of isocitrate or a derivative thereof, and at least one pharmaceutically acceptable carrier, diluent, or excipient, wherein said derivative has the formula

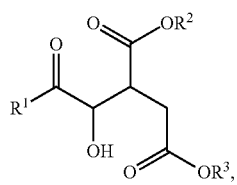

R¹ is —OR⁴; and
R², R³, and R⁴ are independently H, Na, Me, Et, or tBu.

2. The method of claim 1, wherein said composition further comprises erythropoietin.

3. The method of claim 1, wherein the production of red blood cells is stimulated.

4. The method of claim 1, wherein megakaryopoiesis and platelet production is decreased.

5. The method of claim 1, wherein said composition is administered daily.

6. The method of claim 1, wherein the administration is intravenous.

7. The method of claim 1, wherein the administration is intramuscular.

8. The method of claim 1, wherein said subject has anemia of inflammation.

9. The method of claim 1, wherein said subject has anemia of chronic kidney disease.

10. The method of claim 1, wherein said subject is elderly.

11. The method of claim 1, wherein said method stimulates hemoglobin expression.

12. The method of claim 1, wherein said derivative is selected from the group consisting of

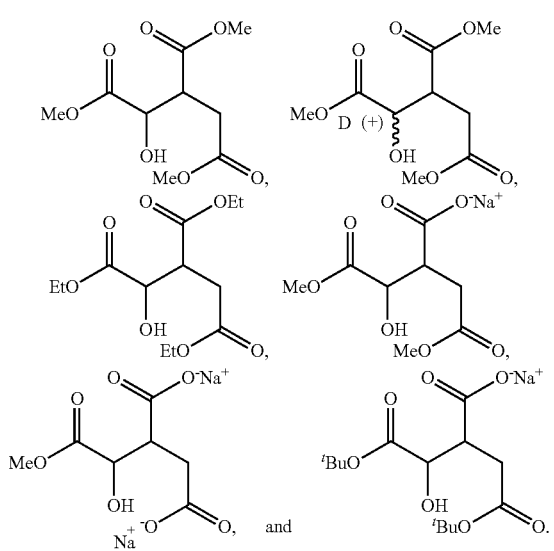

13. The method of claim 12, wherein said derivative is the methyl ester of isocitrate (MIC):

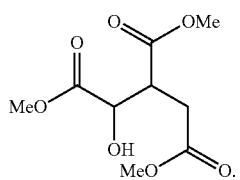 [SMILES: COC(=O)CC(C(=O)OC)C(O)C(=O)OC]

14. The method of claim 1, wherein said therapeutically effective amount is about 10 mg/kg/day.

15. The method of claim 1, wherein said therapeutically effective amount is about 100 mg/kg/day to about 300 mg/kg/day.

16. The method of claim 1, said therapeutically effective amount is selected from about 10 mg/kg/day, 100 mg/kg/day, 200 mg/kd/day, 300 mg/kg/day, 400 mg/kg/day, and 800 mg/kg/day.

* * * * *

SEQUENCE LISTING

<160> NUMBER OF SEQ ID NOS: 2

<210> SEQ ID NO 1
<211> LENGTH: 1959
<212> TYPE: DNA
<213> ORGANISM: Homo sapiens
<220> FEATURE:
<221> NAME/KEY: Misc_Difference
<222> LOCATION: (1874)..(1874)
<223> OTHER INFORMATION: 'T' in cDNA is 'C' in the human genome. The chimpanzee genome agrees with the cDNA sequence, suggesting that this difference is unlikely to be due to an artifact
<220> FEATURE:
<221> NAME/KEY: Misc_Difference
<222> LOCATION: (1913)..(1914)
<223> OTHER INFORMATION: 1 base in the human genome, A, is not found in cDNA. The chimpanzee genome agree with the cDNA sequence, suggesting that this difference is unlikely to be due to an artifact
<220> FEATURE:
<221> NAME/KEY: Misc_Difference
<222> LOCATION: (1925)..(1959)
<223> OTHER INFORMATION: polyA tail: 35 bases do not align to the human genome

<400> SEQUENCE: 1

| | | | | | |
|---|---|---|---|---|---|
| ctgaggcggc | cgaccttcgg | cccgaggcac | cggggcgccg | ggacggcgaa | gatgtcggct | 60 |
| tccttagtcc | gggcaactgt | ccgggctgtg | agcaagagga | agctgcagcc | cacccgggca | 120 |
| gccctcaccc | tgacaccttc | agcagtaaac | aagataaaac | aacttcttaa | agataagcct | 180 |
| gagcatgtag | gtgtaaaagt | tggtgtccga | accaggggct | gtaatggcct | ttcttatact | 240 |
| ctagaatata | caaagacaaa | aggagattct | gatgaagaag | ttattcaaga | tggagtcaga | 300 |
| gtattcatcg | aaaagaaagc | acagctaaca | cttttaggaa | cagaaatgga | ctatgttgaa | 360 |
| gacaaattat | ccagtgagtt | tgtgttcaat | aacccaaaca | tcaaagggac | ttgtggctgt | 420 |
| ggagaaagct | ttaatatttg | aaatctcagg | actcttctgg | ccgtaggttc | caggaaagct | 480 |
| cgtggaagct | ttgggctca | ctgcagaaat | catgtgactg | tcacgtgctg | aaaataaag | 540 |
| tgatacatct | tgaaaatgaa | tccagtgtgt | tggattccag | aagaaatgat | atttatattc | 600 |
| tctataggg | acagaaaatg | agaagccatc | actctttttg | gatcatttag | gtctcttgta | 660 |
| tcctttgttt | tagaaccagt | ttcattaaag | ttgccttcct | gggcacctgt | ttatccattt | 720 |
| cctgaactgt | gtgcactcct | tagatcgcta | ttgatggctt | gatcatccct | cagcatttct | 780 |
| cccaaccaga | tcggtgactc | ctaaaatctg | agacaggaca | tcgtgactgc | tggtagtaat | 840 |
| atggtggtgc | attgttttt | ccacccaaac | ttaacatagc | cttttatac | atttttatga | 900 |
| aaaatttcat | tgtcagctgc | ctcactgcat | actctttaat | agtaccaggc | aaagattttc | 960 |
| ttcaactata | gtacagatta | gttctgagtg | atggtatcaa | aaggtgagaa | agacgtcatc | 1020 |
| cgcctttttt | taatccattt | cttttgccac | cctatatgtc | tgttcagaga | tgggctctca | 1080 |
| agctgacttt | gattctttta | gttgagaagt | ctcttaaagc | catctagccc | acctccatca | 1140 |
| attccctatg | tgaggaagca | aaaccccagg | gaagccaaag | ggctcctgtc | caccctgaca | 1200 |
| ccacaggccg | gggagagta | gggactctac | cccctctcc | ccttgtaggt | gacacatgct | 1260 |
| ctgccctctg | aggcagtcag | cgaaggcaaa | tggtctgact | tctttatgtg | gtcaacattt | 1320 |
| tgatagaatt | tctttataat | ttgatagaga | ttatattatt | tttatttat | ttgagtggg | 1380 |
| aagaattta | aaacctttt | atgtcaatta | ccatcttgtt | tctttcacct | ttgaaacaat | 1440 |
| ggtttgtagc | agagatgaca | ttgtagcaac | ccagaattat | gcttttggaa | tgtggtcctc | 1500 |
| actgtacagg | agaatgtgta | atcttttgtt | aaaattccca | gtgtgcatac | attttctggt | 1560 |

```
tcctcggtcc agttgctaaa gttcttagta ttttagccta acatatttat caccaacttt    1620
tctttaaaag tgttcctttt gtcacttagt tactgatttt cctgggtttg acataagtat    1680
tctatgagat gatatatatg ctttttttga aagctgattc tcatgaattc aagtagctga    1740
gttcctttat gtttcgttta ttcactaaag tagctgacac aaaacacacc aaaacctaga    1800
gcggtagttt tatgtaaatg ctcatgagtt tgtatcaata atataattgt tgatccactt    1860
ataattcgtg caatactgta tgtatgtaga gattgagttg tcaattaaaa aaatgtggcc    1920
tcttaaaaaa aaaaaaaaaa aaaaaaaaaa aaaaaaaa                            1959

<210> SEQ ID NO 2
<211> LENGTH: 129
<212> TYPE: PRT
<213> ORGANISM: Homo sapiens

<400> SEQUENCE: 2

Met Ser Ala Ser Leu Val Arg Ala Thr Val Arg Ala Val Ser Lys Arg
1               5                  10                  15

Lys Leu Gln Pro Thr Arg Ala Ala Leu Thr Leu Thr Pro Ser Ala Val
                20                  25                  30

Asn Lys Ile Lys Gln Leu Leu Lys Asp Lys Pro Glu His Val Gly Val
            35                  40                  45

Lys Val Gly Val Arg Thr Arg Gly Cys Asn Gly Leu Ser Tyr Thr Leu
        50                  55                  60

Glu Tyr Thr Lys Thr Lys Gly Asp Ser Asp Glu Val Ile Gln Asp
65                  70                  75                  80

Gly Val Arg Val Phe Ile Glu Lys Lys Ala Gln Leu Thr Leu Leu Gly
                85                  90                  95

Thr Glu Met Asp Tyr Val Glu Asp Lys Leu Ser Ser Glu Phe Val Phe
                100                 105                 110

Asn Asn Pro Asn Ile Lys Gly Thr Cys Gly Cys Gly Glu Ser Phe Asn
            115                 120                 125

Ile
```